United States Patent [19]

Oda

[11] Patent Number: 4,983,468
[45] Date of Patent: Jan. 8, 1991

[54] METALLIC SLIDE MEMBERS TO BE USED WITH CERAMIC SLIDE MEMBERS AND SLIDING ASSEMBLIES USING THE SAME

[75] Inventor: Isao Oda, Nagoya, Japan
[73] Assignee: NGK Insulators Ltd., Japan
[21] Appl. No.: 326,515
[22] Filed: Mar. 21, 1989

Related U.S. Application Data

[63] Continuation of Ser. No. 70,187, Jul. 6, 1987, abandoned.

[30] Foreign Application Priority Data

Jul. 11, 1986 [JP] Japan ................................ 61-162101

[51] Int. Cl.$^5$ .............................................. B32B 15/04
[52] U.S. Cl. .................................... 428/621; 428/457; 277/DIG. 6; 384/907.1; 384/912
[58] Field of Search ...................... 384/907.1, 912, 913, 384/907; 428/457, 469, 621, 627, 632, 633; 123/188 AA, 143 R, 193 C; 277/DIG. 6

[56] References Cited

U.S. PATENT DOCUMENTS

| | | | |
|---|---|---|---|
| 3,178,241 | 4/1965 | Braunagel | 384/907 |
| 3,641,990 | 2/1972 | Kinnersly | 384/907 |
| 3,711,171 | 1/1973 | Orkin et al. | 384/907.1 |
| 3,808,955 | 5/1974 | Hamada et al. | 123/193 C |
| 4,044,217 | 8/1977 | Otsuki et al. | 123/193 C |
| 4,474,861 | 10/1984 | Ecer | 384/912 |
| 4,522,453 | 6/1985 | Laminar et al. | 384/907 |
| 4,523,554 | 6/1985 | Ryu | 123/193 C |
| 4,632,074 | 12/1986 | Takahashi et al. | 123/188 AA |
| 4,643,144 | 2/1987 | Fingerle et al. | 123/188 AA |
| 4,664,595 | 5/1987 | Tsuji et al. | 384/907 |
| 4,824,262 | 4/1989 | Kamigato et al. | 384/907.1 |

FOREIGN PATENT DOCUMENTS

| | | | |
|---|---|---|---|
| 3435821 | 5/1985 | Fed. Rep. of Germany . | |
| 54-10769 | 1/1979 | Japan | 384/907.1 |
| 13164 | 3/1981 | Japan | 123/188 AA |
| 61-112820 | 5/1986 | Japan | 384/907 |
| 2079869 | 1/1982 | United Kingdom . | |

OTHER PUBLICATIONS

Metal Progress—Databook 1978, pp. 98–99.
Patent Abstracts of Japan, vol. 3, No. 31, p. 97 E 98, Mar. 16, 1979; & JP-A-54 10769 (Suwa Seikosha K.K.) 26-01-1979 European Search Report.
R. L. Mehan et al, "Friction and Wear of Diamond Materials and Other Ceramics Against Metal", General Electric-Corporate Research and Development, Technical Information Series–Class 1, Report No. 80CRD217, Sep. 1980.

*Primary Examiner*—John J. Zimmerman
*Attorney, Agent, or Firm*—Parkhurst, Wendel & Rossi

[57] ABSTRACT

A metallic slide member is disclosed which is advantageously used in combination with an opponent ceramic slide member. The metallic slide member is capable of forming a metal coat lubricating layer on a sliding surface of the ceramic slid member through a metal at a sliding surface of the metallic slide member being transferred onto the ceramic slide member when the metallic slide member slide relative to the ceramic member. Thereby, excellent wear resistance of the metallic slide member can be maintained with respect to the ceramic slide member.

2 Claims, 2 Drawing Sheets

FIG_1
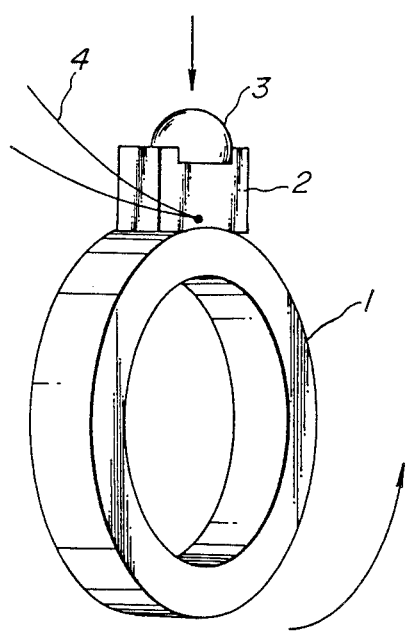

FIG_2
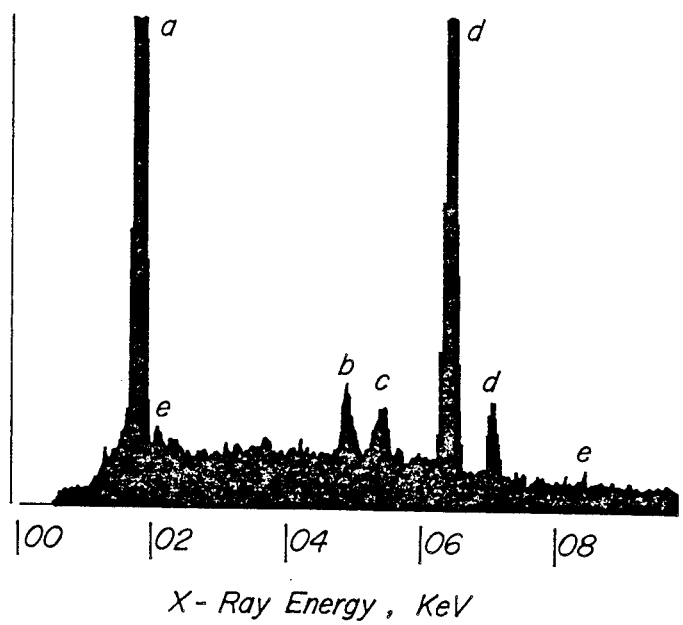
X-Ray Energy, KeV
FIG_3
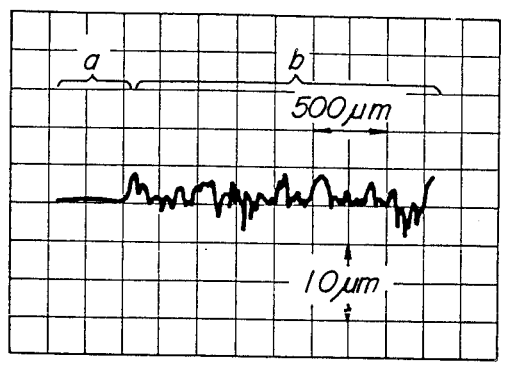

METALLIC SLIDE MEMBERS TO BE USED WITH CERAMIC SLIDE MEMBERS AND SLIDING ASSEMBLIES USING THE SAME

This is a continuation of application Ser. No. 07/070,187 filed Jul. 6, 1987 now abandoned.

BACKGROUND OF THE INVENTION (1) Field of the Invention:

The present invention relates to a sliding assembly consisting of a ceramic member and a metallic member, and the invention particularly relates to a metallic slide member to slide relative to a ceramic member. More particularly, the invention relates to a metallic slide member which transfers its metal to a ceramic member during sliding and exhibits wear resistance by the formation of a metallic coat lubricating layer on the ceramic member without necessitating a surface treatment such as coating, and which preferably contains one or more kinds of alloying elements consisting of Mo, Co, Ti and W in not less than a specific amount.

(2) Related Art Statement:

Ceramics having excellent wear resistance have widely been used as slide members. However, when a ceramic slide member is used, wear of a metallic slide member to slide relative to the ceramic slide member becomes greater. For this reason, in order to improve wear resistance of surfaces of the metallic slide members, the surfaces have been coated by a plasma-sprayed layer or a hard phase has been included in the metal surface layer. For instance, Japanese Patent Application Laid-open No. 62-13,820 discloses that wear resistance of a metallic member to slide relative to silicon nitride, sialon, partially stabilized zirconia, or silicon carbide is improved by coating the metallic member with a mixture of Cu and LiF.

Further, Japanese Patent Application Laid-open No. 59-9,148 discloses a slide member made of a super hard sintered alloy in which a hard phase made of WC is bonded with a binder phase of Co.

However, the former coating method has a disadvantage that the coated layer is likely to peel when it is too thick, while it has a short durable life when it is too thin. On the other hand, the latter sintered alloy has a disadvantage that it is difficult to produce and process and a producing cost is high.

SUMMARY OF THE INVENTION

It is an object of the present invention to obviate the above-mentioned problems, and to provide a metallic member having excellent wear resistance, as a metallic slide member for a ceramic slide member, without necessitating a surface treatment such as coating or inclusion of a hard phase as in the case of the sintered alloy.

It is another object of the present invention to provide a wear resistive sliding assembly consisting of such a metallic slide member and a ceramic slide member.

According to the present invention, there is provided a metallic slide member to be used in combination with a ceramic slide member, wherein the metallic slide member forms a lubricating layer of a metallic coat (hereinafter referred to as "metallic coat lubricating layer") onto a sliding surface of the ceramic slide member by transferring a metal on the sliding surface of the metallic slide member onto the ceramic sliding surface, and which preferably contains one or more kinds of alloying elements consisting of Mo, Co, Ti and W in not less than a specified amount.

According to another aspect of the present invention, there is provided a sliding assembly consisting of a metallic slide member and a ceramic slide member, said metallic slide member being capable of forming a metallic coat lubricating layer on a sliding surface of the ceramic slide member by transferring a metal at a sliding surface of the metallic slide member onto the ceramic member when the metallic slide member slides relative to the ceramic member.

In the conventional metal-ceramic slide assembly, it is known that a metal is transferred upon a slide surface of a ceramic member or vice versa. On the other hand, the metallic slide member according to the present invention is characterized in that a sufficient amount of a metal is transferred to the slide surface of the ceramic slide member to form a metallic coat lubricating layer on the sliding surface of the ceramic slide member.

Thereby, excellent wear resistance can be obtained at room and elevated temperatures.

These and other objects, features and advantages of the present invention will be well appreciated upon reading of the following description of the invention when taken in conjunction with the attached drawings, with understanding that some modifications, variations and changes of the same could be made by the skilled person in the art to which the invention pertains without departing from the spirit of the invention or the scope of the claims appended hereto.

BRIEF DESCRIPTION OF THE ATTACHED DRAWINGS

For a better understanding of the invention, reference is made to the attached drawings, wherein:

FIG. 1 is a schematic view illustrating a sliding mode in a tester used for measurement of a sliding characteristic of a slide member according to the present invention;

FIG. 2 is a diagram of X-ray energy spectrum measured by an energy-dispersive X-ray microanalyzer with respect to a sliding surface of a ceramic test piece having slid in combination with a test sample No. 3 according to the present invention; and FIG. 3 is a diagram showing a surface roughness profile of the ceramic test piece slid in combination with the test sample No. 3 according to the present invention.

DETAILED DESCRIPTION OF THE INVENTION

In the specification and claims, the term "metallic coat lubricating layer" is used to mean a layer of a metal, an oxide of the metal, or a reaction product between the metal and a ceramic material which is firmly stuck to a sliding surface of the ceramic member through physical adsorption or chemical reaction with the ceramic sliding surface as a layer of such a thickness that the transferred layer may prevent the sliding surface of the ceramic slide member from directly contacting with the sliding surface of the opponent metallic slide member and largely reduce wear of the metallic slide member. In actual, the thickness of the transferred layer necessary to function as a lubricating layer is preferably greater than the maximum surface roughness of the sliding surfaces of the metallic slide member and the ceramic slide member. It is preferably that the thickness of the transferred layer is not less than about 0.5 $\mu$m with respect to an ordinarily polished surface. The reason why a metal containing one or more kinds of alloying element consisting of Mo, Co, Ti and W in not less than a specific amount is preferred is that each of Mo, Co, Ti and W has a property of forming a transferred layer upon reaction with a ceramic material.

Since the transfer of the metal upon the ceramic member becomes generally more conspicuous as a temperature becomes higher, the metallic slide member has more excellent wear resistance at higher temperatures.

When the ceramic and metallic members slide relative to each other under the above-mentioned lubrication, a slight solid contact between them may occur to cause wear. For this reason, although the metallic slide member according to the present invention has an excellent sliding characteristic without necessitating a special lubrication, it goes without saying that the invention is also effective under application of an oil lubricant or a solid lubricant.

In the case where there is a possibility that a coating layer of a coated slide member is worn or peels so that a mother metal is locally or entirely brought into contact with an opponent slide member, the metallic slide member according to the present invention is also effective as a substrate metal to be coated.

As compared with the metallic slide member the specific wear amount of the ceramic slide member is indeed smaller. But, the specific wear amount of the ceramic slide member can be reduced to a substantially ignorable degree by the formation of the metal coat lubricating layer according to the present invention.

As ceramic materials of the ceramic slide member in the sliding assembly according to the present invention, silicon nitride, sialon, partially stabilized zirconia and silicon carbide are preferably used.

EXAMPLE 1

FIG. 1 shows a schematic view illustrating a sliding mode of a tester used for measurement of a sliding characteristic of the slide member according to the present invention. A ceramic ring test piece 1 had a ring-like shape of an outer diameter of 35 mm and a width of 8 mm, and its outer peripheral sliding surface was finished to an average sliding surface roughness of 0.2 $\mu$m. A metallic test piece 2 had a block-like shape of 16 mm $\times$ 10 mm $\times$ 6 mm, and its sliding surface was finished to a sliding surface roughness of 0.1 to 0.2 $\mu$m. A load of 20 N was downwardly applied upon the metallic test piece 2 by way of a spherical seat 3 by means of a fulcrum type loader (not shown). A sliding test was performed in a dry state in air while the ceramic ring test piece was rotated at 1,450 rpm (a peripheral speed: 2.7 m/s). In a high temperature test, an atmosphere around a sliding section was heated in an electric furnace, and a temperature was measured by a thermocouple 4 spot welded to the surface of the metallic test piece 2 spaced from the sliding surface by 1 mm. A room temperature test was performed without being heated by the electric furnace, but a temperature at the thermocouple 4 was about 150° C. due to generation of a frictional heat.

With respect to pressurelessly sintered silicon nitride among ceramic materials and various metallic materials shown in the following Table 1, sliding tests were carried out by using the above-mentioned tester, and coefficients of friction during sliding and specific wear rates after sliding over a specific distance were measured. Results were shown in Table 2a. Results regarding respective alloy components are given in Tables 2b to 2e, respectively. It is understood from Table 2b that if Mo is contained in an amount of not less than 32 wt%, a practically sufficient specific wear rate of not more than $10^{-8}$ mm$^2$/N can be obtained. Further, it is also understood from Tables 2c, 2d and 2e that when Co, Ti or W is contained in an amount of not less than 20 wt %, not less than 84 wt %, and not less than 5 wt %, respectively, the specific wear rate is not more than $10^{-8}$ mm$^2$/N. The specific wear rates of the metallic members outside the scope of the present invention are all as much as not less than $10^{-8}$ mm$^2$/N.

EXAMPLE 2

By using the same sliding tester and experimental conditions as in Example 1, sliding tests were carried out with respect to combinations of M2 steel which exhibited good sliding characteristic in Example 1 and various ceramics or with respect to a combination of M2 steel and silicon nitride when Cu+PbO were plasma sprayed onto the sliding surface of the M2 steel as a solid lubricant. Results are shown in Table 3. The specific wear rate of M2 steel was not more than $10^{-8}$ mm$^2$/N with respect to any of the ceramics. Further, the M2 steel coated with Cu+PbO had a smaller specific wear rate as compared with a non-treated M2 steel.

FIG. 2 shows a measurement result of X-ray energy spectrum of a sliding surface of a ceramic test piece slid in combination with a sample No. 33 according to the present invention by using an energy-dispersive X-ray microanalyzer. This spectrum was obtained under conditions that an energy of an incident electrons was 20 keV and an irradiated area was 1 $\mu$m$\Phi$. In FIG. 2, "a", "b", "c", "d", and "e" correspond to X-rays due to Si element, Ce element, Cr element, Fe element, and W element, respectively. As obvious from the spectrum thus obtained, Fe, Cr and W are alloying elements of M2, and a sufficient amount of M2 steel was transferred to the ceramics. Si is an element contained in Si$_3$N$_4$. CeO$_2$ was used as a sintering aid for Si$_3$N$_4$ and Ce is an element constituting an intergranular phase.

FIG. 3 shows a profile of the surface roughness of a ceramic test piece slid in combination with the test sample No. 33 according to the present invention. In FIG. 3, "a" and "b" are a non-slid area and a sliding surface area, respectively. As obvious from this figure, the surface roughness of the sliding surface "b" increased due to wear, but a plurality of areas higher by 2 to 4 $\mu$m than the non-slid area "a" exists, which shows that the metal was transferred onto the ceramics.

Table 3 gives increased weights of the slid ceramic test pieces due to the transfer. The increased weight being 0 mg means that the wear amount is equal to the transferred amount.

As evident from the foregoing explanation, since the metallic slide member according to the present invention forms a metallic coat lubricating layer onto the ceramic sliding surface through a metal being transferred onto the sliding surface of the ceramic slide member, it can exhibit excellent wear resistance at room temperature as well as particularly at elevated temperatures.

Further, the metallic slide member according to the present invention is featured by more facilitated manufacturing and processing and less expensive cost as compared with the conventional surface-coating method. Thus, the present invention can favorably be applied to parts combinations of a cylinder liner and a piston ring, a valve and a valve seat, a tappet or a rocker arm tip and a cam, etc.

TABLE 1

| | Abbreviation | Material (composition wt %) | Hardness (GPa) |
|---|---|---|---|
| | SN | Pressurelessly sintered silicon nitride | 15 |
| | SA | Pressurelessly sintered sialon | 14 |
| | PSZ | Pressurelessly sintered partially stabilized zirconia containing $Y_2O_3$ | 12 |
| | SC | Pressurelessly sintered silicon carbide | 28 |
| Present invention | Mo | Mo | 2.8 |
| | Ti 318 | Ti—6Al, 4V | 3.5 |
| | Ti 371 | Ti—2.5Al, 13.5Si | 3.8 |
| | Tribaloy 700 | Ni—15Cr, 32Mo, 3Si | 5.2 |
| | Trobaloy 100 | Co—35Mo, 10Si | 4.3 |
| | Haynes 25 | Co—20Cr, 10Ni, 15W, 3Fe, 0.1C | 3.3 |
| | Nimonic 91 | Ni—28Cr, 20Co, 0.1C, 1Al, 1Nb | 4.0 |
| | M2 | Fe—0.8C, 4Cr, 6W, 5Mo, 2V | 9.5 |
| | Stellite 1 | Co—32Cr, 12.5W, 2.4C, 0.6Si, 2.3Fe, 2.3Ni, 0.2Mo | 6.4 |
| | Stellite 6 | Co—29Cr, 4W, 1.1C, 1.2Si, 2.3Fe, 2.6Ni | 4.5 |
| Outside present invention | Incoloy 625 | Ni—21Cr, 9Mo, 2.5Fe, 3Cb | 2.5 |
| | Incoloy 617 | Ni—22Cr, 12Co, 9Mo, 1.2Al, 1.5Fe | 2.4 |
| | SUS 316 | Fe—0.08C, 17Cr, 12Ni, 2.5Mo | 1.8 |
| | R 41 | Ni—19Cr, 11Co, 10Mo, 5Fe, 0.1C | 3.2 |
| | Hasteloy X | Ni—22Cr, 9Mo, 19Fe, 1.5Co, 0.6W, 0.1C | 2.2 |

TABLE 2(a)

| | | Test piece Metal | Test piece Ceramics | Temperature (°C.) | Slid distance (km) | Coefficient of friction | Specific wear rate ($mm^2/N$) | Ceramics weight change (mg) |
|---|---|---|---|---|---|---|---|---|
| Present invention | No. 1 | Mo | SN | 600 | 165 | 0.45 | $4 \times 10^{-9}$ | −1 |
| | No. 2 | Mo | SN | RT | 165 | 0.35 | $2 \times 10^{-9}$ | +1.5 |
| | No. 3 | Ti 318 | SN | 600 | 165 | 0.50 | $4 \times 10^{-9}$ | +2 |
| | No. 4 | Ti 318 | SN | RT | 165 | 0.35 | $1 \times 10^{-9}$ | +11.5 |
| | No. 5 | Ti 371 | SN | 600 | 165 | 0.40 | $3 \times 10^{-9}$ | +8 |
| | No. 6 | Tribaloy 700 | SN | 600 | 165 | 0.25 | $4 \times 10^{-9}$ | +9 |
| | No. 7 | Tribaloy 100 | SN | 600 | 165 | 0.30 | $6 \times 10^{-9}$ | +3 |
| | No. 8 | Haynes 25 | SN | 600 | 165 | 0.45 | $7 \times 10^{-9}$ | −2 |
| | No. 9 | Nimonic 91 | SN | 600 | 165 | 0.50 | $9 \times 10^{-9}$ | +2 |
| | No. 10 | M2 | SN | RT | 165 | 0.50 | $7 \times 10^{-9}$ | 0 |
| | No. 11 | M2 | SN | 400 | 165 | 0.45 | $4 \times 10^{-9}$ | +1 |
| | No. 12 | M2 | SN | 600 | 165 | 0.45 | $9 \times 10^{-10}$ | +3 |
| | No. 13 | Stellite 1 | SN | RT | 165 | 0.40 | $6 \times 10^{-9}$ | 0 |
| | No. 14 | Stellite 1 | SN | 400 | 165 | 0.35 | $3 \times 10^{-9}$ | +2 |
| | No. 15 | Stellite 1 | SN | 600 | 165 | 0.30 | $2 \times 10^{-9}$ | +3 |
| | No. 16 | Stellite 6 | SN | 600 | 165 | 0.40 | $4 \times 10^{-9}$ | +2 |
| Outside present invention | No. 17 | Incoloy 625 | SN | 600 | 165 | 0.45 | $3.3 \times 10^{-8}$ | −3 |
| | No. 18 | Incoloy 617 | SN | 600 | 165 | 0.40 | $4.4 \times 10^{-8}$ | −2 |
| | No. 19 | SUS 316 | SN | 600 | 165 | 0.50 | $2.8 \times 10^{-8}$ | −2 |
| | No. 20 | R 41 | SN | 600 | 165 | 0.45 | $1.9 \times 10^{-8}$ | −10 |
| | No. 21 | Hasteloy X | SN | 600 | 165 | 0.50 | $1.2 \times 10^{-8}$ | −5 |

TABLE 2(b)

Mo series

| | | Test piece Metal | Temperature (°C.) | Slid distance (km) | Coefficient of friction | Specific wear rate ($mm^2/N$) | Ceramics weight change (mg) | Mo content (wt %) |
|---|---|---|---|---|---|---|---|---|
| Present invention | No. 1 | Mo | 600 | 165 | 0.45 | $4 \times 10^{-9}$ | −1 | 100 |
| | No. 2 | Mo | RT | 165 | 0.35 | $2 \times 10^{-9}$ | +1.5 | 100 |
| | No. 6 | Tribaloy 700 | 600 | 165 | 0.25 | $4 \times 10^{-9}$ | +9 | 32 |
| | No. 7 | Tribaloy 100 | 600 | 165 | 0.30 | $6 \times 10^{-9}$ | +3 | 35 |
| Outside present invention | No. 16 | Incoloy 625 | 600 | 165 | 0.45 | $3.3 \times 10^{-8}$ | −3 | 9 |
| | No. 17 | Incoloy 617 | 600 | 165 | 0.40 | $4.4 \times 10^{-8}$ | −2 | 9 |
| | No. 18 | SUS 316 | 600 | 165 | 0.50 | $2.8 \times 10^{-8}$ | −2 | 10 |
| | No. 19 | R 41 | 600 | 165 | 0.45 | $1.9 \times 10^{-8}$ | −10 | 9 |

TABLE 2(c)

Co series

| | | Test piece Metal | Temperature (°C.) | Slid distance (km) | Coefficient of friction | Specific wear rate ($mm^2/N$) | Ceramics weight change (mg) | Co content (wt %) |
|---|---|---|---|---|---|---|---|---|
| Present invention | No. 7 | Tribaloy 700 | 600 | 165 | 0.30 | $6 \times 10^{-9}$ | +3 | 55 |
| | No. 8 | Haynes 25 | 600 | 165 | 0.45 | $7 \times 10^{-9}$ | −2 | 52 |
| | No. 9 | Nimonic 91 | 600 | 165 | 0.50 | $9 \times 10^{-9}$ | +2 | 20 |

TABLE 2(c)-continued

Co series

|  |  | Test piece Metal | Temperature (°C.) | Slid distance (km) | Coefficient of friction | Specific wear rate (mm²/N) | Ceramics weight change (mg) | Co content (wt %) |
| --- | --- | --- | --- | --- | --- | --- | --- | --- |
|  | No. 13 | Stellite 1 | RT | 165 | 0.40 | $6 \times 10^{-9}$ | 0 | 49.7 |
|  | No. 14 | Stellite 1 | 400 | 165 | 0.35 | $3 \times 10^{-9}$ | +2 | 49.7 |
|  | No. 15 | Stellite 1 | 600 | 165 | 0.30 | $2 \times 10^{-9}$ | +3 | 49.7 |
|  | No. 16 | Stellite 6 | 600 | 165 | 0.40 | $4 \times 10^{-9}$ | +2 | 59.8 |
| Outside | No. 17 | Incoloy 617 | 600 | 165 | 0.40 | $4.4 \times 10^{-8}$ | −2 | 12 |
| present | No. 19 | R 41 | 600 | 165 | 0.45 | $1.9 \times 10^{-8}$ | −10 | 11 |
| invention | No. 20 | Hasteloy X | 600 | 165 | 0.50 | $1.2 \times 10^{-8}$ | −5 | 1.5 |

TABLE 2(d)

W series

|  |  | Test piece Metal | Temperature (°C.) | Slid distance (km) | Coefficient of friction | Specific wear rate (mm²/N) | Ceramics weight change (mg) | W content (wt %) |
| --- | --- | --- | --- | --- | --- | --- | --- | --- |
| Present | No. 10 | M2 | RT | 165 | 0.50 | $7 \times 10^{-9}$ | 0 | 5 |
| invention | No. 11 | M2 | 400 | 165 | 0.45 | $4 \times 10^{-9}$ | +1 | 5 |
|  | No. 12 | M2 | 600 | 165 | 0.45 | $9 \times 10^{-10}$ | +3 | 5 |
| Outside present invention | No. 20 | Hasteloy X | 600 | 165 | 0.50 | $1.2 \times 10^{-8}$ | −5 | 0.6 |

TABLE 2(e)

Ti series

|  |  | Test piece Metal | Temperature (°C.) | Slid distance (km) | Coefficient of friction | Specific wear rate (mm²/N) | Ceramics weight change (mg) | Ti content (wt %) |
| --- | --- | --- | --- | --- | --- | --- | --- | --- |
| Present | No. 3 | Ti 318 | 600 | 165 | 0.50 | $4 \times 10^{-9}$ | +2 | 90 |
| invention | No. 4 | Ti 318 | RT | 165 | 0.35 | $1 \times 10^{-9}$ | +11.5 | 90 |
|  | No. 5 | Ti 371 | 600 | 165 | 0.40 | $3 \times 10^{-9}$ | +8 | 84 |

TABLE 3

| Test piece | | Temperature (°C.) | Slid distance (km) | Coefficient of friction | Specific wear rate (mm²/N) | Ceramics weight change (mg) |
| --- | --- | --- | --- | --- | --- | --- |
| Metal | Ceramics | | | | | |
| No. 31 | M2 | SN | RT | 165 | 0.50 | $7 \times 10^{-9}$ | 0 |
| No. 32 | M2 | SN | 400 | 165 | 0.45 | $4 \times 10^{-9}$ | +1 |
| No. 33 | M2 | SN | 600 | 165 | 0.45 | $9 \times 10^{-10}$ | +3 |
| No. 34 | M2 | PSZ | RT | 165 | 0.45 | $5 \times 10^{-9}$ | 0 |
| No. 35 | M2 | PSZ | 600 | 165 | 0.40 | $2 \times 10^{-9}$ | +4 |
| No. 36 | M2 | SA | RT | 165 | 0.45 | $6 \times 10^{-9}$ | +1 |
| No. 37 | M2 | SA | 600 | 165 | 0.45 | $8 \times 10^{-10}$ | +3 |
| No. 38 | M2 | SC | RT | 165 | 0.40 | $8 \times 10^{-9}$ | 0 |
| No. 39 | M2 | SC | 600 | 165 | 0.35 | $1 \times 10^{-9}$ | 0 |
| No. 40 | M2 + Cu, PbO | SN | 600 | 165 | 0.27 | $7 \times 10^{-10}$ | +4 |

What is claimed is:

1. A metallic slide member in sliding juxtaposition with a sliding surface of a ceramic member wherein said metallic slide member is capable of forming a metallic lubricating layer on the sliding surface of the ceramic member, whereby when the metallic slide member slides on the sliding surface of said ceramic member, metal is transferred from the metallic slide member to the sliding surface of the ceramic member thereby forming a metallic coat lubricating layer on the sliding surface of the ceramic member, said metallic slide member being made of at least one metallic material selected from the group consisting of Ti-6A1-4V, Ti-2.5A1-13.5Sn, Co-35Mo-10Si, Ni-15Cr-32Mo-3Si, Co-20Cr-10Ni-15W-3Fe-0.1C, Ni-28Cr-20Co-0.1C-2Ti-1A1-1Nb, Fe-0.8C-4Cr-6W-5Mo-2V, Co-32Cr-12.5W-2.4C-0.6Si-2.3Fe-2.3Ni-0.2Mo, Co-29Cr-4W-1.1C-1.2Si-2.3Fe-2.6Ni, and Mo as expressed by weight % in composition.

2. A sliding assembly consisting of a metallic slide member and a ceramic slide member in sliding juxtaposition, wherein said metallic slide member is capable of forming a metallic lubricating layer on the sliding surface of the ceramic member, whereby when the metallic slide member slides on the sliding surface of said ceramic member, metal is transferred from the metallic slide member to the sliding surface of the ceramic member thereby forming a metallic coat lubricating layer on the sliding surface of the ceramic member, said metallic slide member being made of at least one metallic material selected from the group consisting of Ti-6A1-4V, Ti-2.5A1-13.5Sn, Co-35Mo-10Si, Ni-15Cr-32Mo-3Si, Co-20Cr-10Ni-15W-3Fe-0.1C, Ni-28Cr-20Co-0.1C-2Ti-1A1-1Nb, Fe-0.8C-4Cr-6W-5Mo-2V, Co-32Cr-12.5W-2.4C-0.6Si-2.3Fe-2.3Ni-0.2Mo, Co-29Cr-4W-1.1C-1.2Si-2.3Fe-2.6Ni, and Mo as expressed by weight % in composition.

* * * * *